United States Patent [19]

Allen, Jr. et al.

[11] 4,230,705
[45] Oct. 28, 1980

[54] 6-PHENYL-1,2,4-TRIAZOLO[4,3-b]PYRIDAZINES AND THEIR USES IN TREATING ANXIETY

[75] Inventors: George R. Allen, Jr., Old Tappan, N.J.; John W. Hanifin, Jr.; Daniel B. Moran, both of Suffern, N.Y.; Jay D. Albright, Nanuet, N.Y.

[73] Assignee: American Cyanamid Company, Stamford, Conn.

[21] Appl. No.: 725,597

[22] Filed: Sep. 22, 1976

[51] Int. Cl.³ .................. C07D 487/04; A61K 31/50; C07D 237/14
[52] U.S. Cl. .................................... 424/250; 544/236; 544/244; 544/239
[58] Field of Search ................. 260/250 AC; 424/250; 544/236

[56] References Cited

FOREIGN PATENT DOCUMENTS 1187281   4/1970   United Kingdom ............. 260/250 AC

OTHER PUBLICATIONS

Deev, et al., Chem. Abs. 82, 125338r (1973).
Yurugi et al., Chem. Abs. 80, 37073d (1973).
Leclerc et al., Bull. Soc. Chim. France.

*Primary Examiner*—Mark L. Berch
*Attorney, Agent, or Firm*—Edward A. Conroy, Jr.

[57] ABSTRACT

This disclosure describes novel substituted 6-phenyl-1,2,4-triazolo[4,3-b]pyridazines useful as anxiolytic agents.

2 Claims, No Drawings

6-PHENYL-1,2,4-TRIAZOLO[4,3-b]PYRIDAZINES AND THEIR USE IN TREATING ANXIETY

BRIEF SUMMARY OF THE INVENTION

This invention relates to new organic compounds and, more particularly, is concerned with novel substituted 6-phenyl-1,2,4-triazolo[4,3-b]pyridazines which may be represented by the following structural formula:

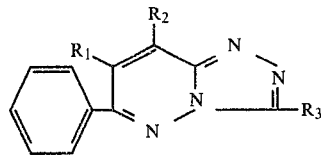

wherein $R_1$, $R_2$, and $R_3$ are each individually selected from the group consisting of hydrogen and alkyl having up to four carbon atoms with the first proviso that when $R_1$ and $R_2$ are both hydrogen then $R_3$ may not be methyl and with the second proviso that when $R_2$ and $R_3$ are both methyl then $R_1$ may not be hydrogen. The invention also includes novel compositions of matter containing the above-defined compounds useful as anxiolytic agents and the method of meliorating anxiety in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, dimethylformamide, acetone, chloroform, ethyl acetate, and the like. They are appreciably soluble in non-polar organic solvents such as toluene, carbon tetrachloride, and the like but are relatively insoluble in water. The organic bases of this invention form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention may be readily prepared in accordance with the following reaction scheme:

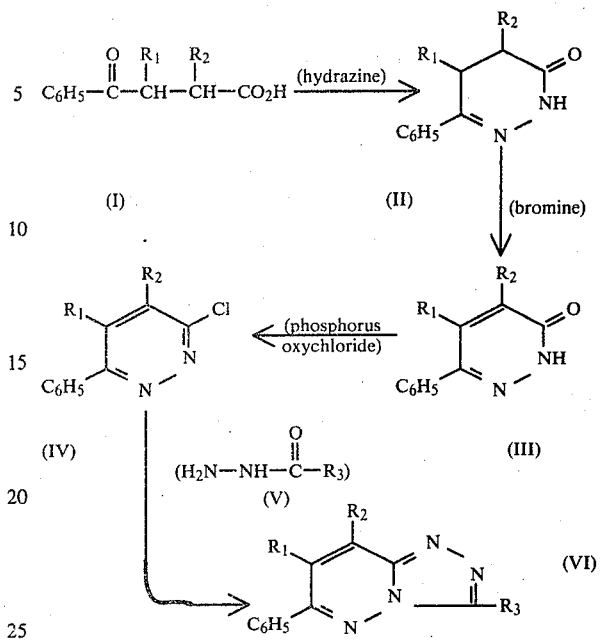

wherein $R_1$, $R_2$, and $R_3$ are each individually hydrogen or alkyl having up to four carbon atoms. In accordance with the above reaction scheme, an appropriately substituted 3-benzoylpropionic acid (I) is reacted with hydrazine hydrate at the reflux temperature in a lower alkanol solvent for a period of 12-24 hours to provide the corresponding 4,5-dihydro-6-phenyl-3(2H)-pyridazinone (II). Treatment of the 4,5-dihydro-6-phenyl-3(2H)-pyridazinone (II) with bromine in glacial acetic acid solvent at steam bath temperature for a period of 2-4 hours provides the corresponding 6-phenyl-3(2H)-pyridazinone (III). Conversion of the 6-phenyl-3(2H)-pyridazinone (III) to the corresponding 3-chloro-6-phenylpyridazine (IV) is achieved by treatment with excess phosphorus oxychloride at steam bath temperature for a period of 4-8 hours. Interaction of the 3-chloro-6-phenylpyridazine (IV) with an acylhydrazine (V) at the reflux temperature in a lower alkanol solvent for a period of 24-48 hours provides the corresponding 6-phenyl-1,2,4-triazolo[4,3-b]pyridazines (VI) of the present invention.

The novel compounds of the present invention possess central nervous system activity at non-toxic doses and as such are useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention have been established in a test which indicates anxiolytic activity by the measure of protection from convulsions resulting from the administration of pentylenetetrazole. Graded dose levels of the compounds of this invention were administered orally, in a 2% starch vehicle, to groups of at least 5 rats. At the estimated time of peak effect, the rats were treated intravenously with pentylenetetrazole at a dose of 21 to 23 mg./kg. of body weight. This dose is estimated to cause clonic seizures in 99% of unprotected rats. The effective dose ($ED_{50}$) of the test compound for protection of 50% of the animals is calculated by the method of D. H. Finney in "Statistical Methods in Biological Assay", Second Edition, Hafner Publishing Co., New York, 1964, pp. 456–457. Representative results are given in Table I which follows in comparison with chlordiazepoxide or meprobamate, which were tested in exactly the same manner. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals.

TABLE I

Protection Against Clonic Seizures Caused By Pentylenetetrazole in Rats

| Compound | Medium Effective Oral Dose mg./kg. $ED_{50}$ |
|---|---|
| 3-Methyl-6-phenyl-1,2,4-triazolo[4,3-b]pyridazine | 3 |
| Chlordiazepoxide | 2.5 |
| Meprobamate | 22 |
| 6-Phenyl-1,2,4-triazole-[4,3-b]pyridazine | 9, 5 |

Another test which has been used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, Vol. 21, pp. 1–7 (1971). A conflict situation is induced in rats by a modification of this method. To groups of six naive Sprague-Dawley rats (200–220 grams), previously deprived of water for forty-eight hours and food for 24 hours, are administered graded oral doses of test compound suspended in 2% starch vehicle also containing 2 drops of polyethylene glycol and polysorbate 80, or vehicle alone (controls). At the time of peak effect each rat is placed in a plexiglass box fitted with a drinkometer circuit connected between the stainless steel grid floor and a stainless steel drinking tube inserted in a hole in one of the walls of the box. A stimulator supplying monophasic 60 cycle square wave pulses of 0.2 milliamperes peak intensity, a timer which allows alternate 5 second "shock free" and 5 second "shock available" periods during a 5 minute test period, an electromagnetic counter to count the number of shocks received by the rat during the shock available period and a delay of one half second between the successive shocks are incorporated into the drinkometer circuit. After the rat is placed in the box, it is allowed to explore and drink 10% dextrose solution supplied through the tap. After twenty seconds of continuous unpunished drinking, the timer and drinkometer circuits are activated and 5 second shock free and 5 second shock available periods alternate. The number of shocks received by the rat during a 5 minute test period is recorded. The percentage of rats that receive 9 or more shocks in 4 to 5 minutes at each dose level is used as positive response in calculation of the median effective dose ($ED_{50}$). The results of this test on representative compounds of this invention appear in Table II below.

TABLE II

| Compound | Median Effective Dose ($ED_{50}$ mg./kg.) |
|---|---|
| 3-Methyl-6-phenyl-1,2,4-triazolo[4,3-b]pyridazine | 100 |
| Chlordiazepoxide | 9.6 |
| Meprobamate | 51.9 |

The novel compounds of the present invention have been found to be highly useful for meliorating anxiety in mammals when administered in amounts ranging from about 0.03 milligram to about 10.0 mg. per kilogram of body weight per day. A preferred dosage regimen for optimum results would be from about 0.1 mg. to about 5.0 mg. per kilogram of body weight per day, and such dosage units are employed that a total of from about 7.0 milligram to about 0.35 gram of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-$\alpha$- glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 to 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

| Preparation of 50 mg. Tablets | | |
| --- | --- | --- |
| Per Tablet | | Per 10,000 Tablets |
| 0.050 gm. | 7,8-Triethyl-6-phenyl-1,2,4-triazolo[4,3-b]pyridazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 3,7,8-triethyl-6-phenyl-1,2,4-triazolo[4,3-b]pyridazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 2

| Preparation of Oral Suspension | |
| --- | --- |
| Ingredient | Amount |
| 3,8-Di-n-butyl-6-phenyl-1,2,4-triazolo[4,3-b]pyridazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the 3,8-di-n-butyl-6-phenyl-1,2,4-triazolo[4,3-b]pyridazine is suspended therein. The saccharin, sodium benzoate, flavor and dye are added and dissolved. The volume is adjusted to 100 ml. with distilled water. Each ml. of syrup contains 5 mg. of 3,8-di-n-butyl-6-phenyl-1,2,4-triazolo[4,3-b]pyridazine.

EXAMPLE 3

Preparation of Parenteral Solution

In a solution of 700 ml. of propylene glycol and 200 ml. of water for injection is suspended 20.0 grams of 7,8-di-n-propyl-6-phenyl-1,2,4-triazolo[4,3-b]pyridazine monohydrochloride with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 4

Preparation of 3,7,8-trimethyl-6-phenyl-1,2,4-triazolo[4,3-b]pyridazine

A 200 g. portion of 3-benzoyl-2,3-dimethyl-propionic acid and 60 g. of hydrazine hydrate are added to one liter of ethyl alcohol and stirred at reflux for 18 hours. The reaction mixture is then cooled in an ice bath and collected in a conventional manner to afford 4,5-dihydro-4,5-dimethyl-6-phenyl-3(2H)-pyridazinone as a cream colored solid. This product is partially dissolved in 600 ml. of glacial acetic acid. To this is added, portionwise, a solution of 50 ml. of bromine in 100 ml. of glacial acetic acid, while warming on a steam bath (approximately 15% of the bromine solution is added to the reaction mixture before warming is started and about one hour is required to complete the addition during which time quantities of hydrogen bromide gas are given off). After the addition is completed, the reaction mixture is heated on the steam bath for one hour, and then the mixture is poured onto crushed ice. The resulting solid is vacuum filtered, washed copiously with water, and air dried to give 4,5-dimethyl-6-phenyl-3(2H)-pyridazinone as a cream colored solid. This material is added to 800 ml. of phosphorus oxychloride and is heated on a steam bath for 5 hours. The reaction mixture is concentrated to remove the excess phosphorus oxychloride and is then diluted with cold water. The resulting solid is vacuum filtered, washed copiously with water, and air dried to give 3-chloro-4,5-dimethyl-6-phenylpyridazine as a pinkish solid. A 10 g. portion of this product plus 8 g. of N-acetylhydrazine and 100 ml. of n-butyl alcohol is allowed to stir at reflux for 48 hours. The reaction mixture is cooled in an ice bath and the resulting solid is vacuum filtered, washed first with petroleum ether and then with water, and is air dried. The solid is recrystallized from ethyl alcohol after treatment with activated charcoal and is dried in vacuo to give 3,7,8-trimethyl-6-phenyl-1,2,4-triazolo[4,3-b]pyridazine as a white solid.

EXAMPLE 5

Preparation of 7-methyl-6-phenyl-1,2,4-triazolo[4,3-b]pyridazine

A 10 g. portion of 6-(p-bromophenyl)-5-methyl-3(2H)-pyridazinone [J. Medicinal Chem. 17, 281 (1974)] and 100 ml. of phosphorus oxychloride are heated at steam bath temperature for 3 hours. The mixture is added dropwise to cold water while stirring. The resulting solid is filtered and washed with water to afford 3-(p-bromophenyl)-6-chloro-4-methyl pyridazine as a grey solid. A mixture of 1.5 g. of this compound, 0.64 g. of formylhydrazine and 25 ml. of n-butyl alcohol is stirred at reflux for 18 hours. The reaction mixture is cooled in an ice bath, filtered, and the solid is recrystallized from methyl alcohol giving 6-(p-bromophenyl)-7-methyl-1,2,4-triazolo[4,3-b]pyridazine.

A mixture of 10 g. of the above material, 30 ml. of ammonium hydroxide, 250 ml. of ethyl alcohol and a catalytic amount of 10% palladium on charcoal is shaken in a Parr shaker for 18 hours. The uptake of 35 pounds of hydrogen is complete in 2 hours. The reaction mixture is then filtered to remove the catalyst and the filtrate is concentrated to a white solid which is triturated with petroleum ether. The solid is collected by filtration, air dried and recrystallized from methanol-ethyl acetate to give 7-methyl-6-phenyl-1,2,4-triazolo[4,3-b]pyridazine as white crystals, m.p. 188°–190° C.

EXAMPLE 6

Preparation of 3-methyl-6-phenyl-1,2,4-triazolo[4,3-b]pyridazine

The title compound is prepared by the method of Duffin et al. as set forth in British Pat. No. 839,020 issued on June 29, 1960.

EXAMPLE 7

Preparation of 3,8-dimethyl-6-phenyl-1,2,4-triazolo[4,3-b]pyridazine

The title compound is prepared by the method of Leclerc & Wermuth as set forth in Bull. Soc. Chim. France, No. 5, 1752 (1971).

EXAMPLE 8

Preparation of 7-isopropyl-6-phenyl-1,2,4-triazolo[4,3-b]pyridazine

The procedure of Example 4 is repeated substituting equimolecular amounts of 3-benzoyl-3-isopropyl-propionic acid and N-formylhydrazine for the 3-benzoyl-2,3-dimethyl-propionic acid and N-acetylhydrazine employed in that example. There is thus obtained the title compound in equally good yield.

EXAMPLE 9

Preparation of 8-isobutyl-6-phenyl-1,2,4-triazolo[4,3-b]pyridazine

Following the general procedure of Example 4, 3-benzoyl-2-isobutyl-propionic acid is converted to 3-chloro-4-isobutylpyridazine which is treated with N-formylhydrazine to give the title compound.

EXAMPLE 10

Preparation of 3-ethyl-7-methyl-6-phenyl-1,2,4-triazolo[4,3-b]pyridazine

The general procedure of Example 4 is repeated but replacing the 3-benzoyl-2,3-dimethyl-propionic acid and N-acetylhydrazine employed in that example with 3-benzoyl-3-methyl-propionic acid and N-propionylhydrazine.

EXAMPLE 11

Preparation of 6-phenyl-1,2,4-triazolo[4,3-b]pyridazine

A 10 g. portion of 3-chloro-6-phenylpyridazine (Chem. Abs., 44, 5616i), 6.6 g. of formylhydrazine and 100 ml. of n-butanol are refluxed for 48 hours. The reaction mixture is cooled in an ice bath. The resulting solid is filtered, washed with petroleum ether and water and air dried giving 6-phenyl-1,2,4-triazolo[4,3-b]pyridazine as tan crystals, m.p. 138°–139° C.

EXAMPLE 12

Preparation of 8-methyl-6-phenyl-1,2,4-triazolo[4,3-b]pyridazine

A mixture of 13.2 g. of 4-methyl-6-phenyl-3(2H)-pyridazinone and 200 ml. of phosphorus oxychloride is heated on a steam bath for 18 hours. The reaction mixture is filtered. The filtrate is concentrated free of excess phosphorus oxychloride. The residue is stirred with ice water and filtered. The solid is washed with water and air dried giving 3-chloro-4-methyl-6-phenylpyridazine as a cream colored solid.

A mixture of 2.05 g. of the above product, 1.2 g. of formylhydrazine and 50 ml. of n-butanol is stirred and refluxed for 48 hours. The reaction mixture is concentrated free of solvent and the residue is stirred with diethyl ether. The mixture is filtered giving a cream colored solid. This solid is recrystallized from methanol after treatment with activated charcoal. The methanol filtrate is allowed to evaporate slowly at room temperature resulting in the formation of white needles along with a dark yellow oil. The oil is removed and the needles are washed with a small amount of diethyl ether which is decanted. The needles are then recrystallized from methanol-diethyl ether-petroleum ether giving 8-methyl-6-phenyl-1,2,4-triazolo[4,3-b]pyridazine as white crystals, m.p. 150°–151° C.

EXAMPLE 13

Preparation of 3-n-propyl-6-phenyl-1,2,4-triazolo[4,3-b]pyridazine

A mixture of 10 g. of 3-chloro-6-phenylpyridazine, 11.2 g. of butyric acid hydrazide and 100 ml. of n-butanol is heated at reflux for 40 hours. The solution is cooled and the precipitate is filtered and washed with petroleum ether and water. The filtrate is concentrated to an oil which forms a precipitate upon the addition of petroleum ether. The precipitate is collected and washed with petroleum ether and water. The solids are combined and recrystallized from 30 ml. of ethanol giving 3-n-propyl-6-phenyl-1,2,4-triazolo[4,3-b]pyridazine as crystals, m.p. 123°–125° C.

EXAMPLE 14

Preparation of 3-ethyl-6-phenyl-1,2,4-triazolo[4,3-b]pyridazine

A mixture of 7.6 g. of 3-chloro-6-phenylpyridazine, 7.4 g. of propionic acid hydrazide and 60 ml of n-butanol is stirred at reflux temperature for 48 hours. The solution is cooled in a chilled room, concentrated to remove the solvent and triturated with water giving crystals. The mixture is filtered, washed with petroleum ether and water and dried. The product is recrystallized from 20 ml. of ethanol giving 3-ethyl-6-phenyl-1,2,4-triazolo[4,3-b]pyridazine, m.p. 133°–135° C.

We claim:

1. The method of meliorating anxiety in a mammal which comprises administering internally to said mammal an effective amount of a compound selected from the group consisting of those of the formula:

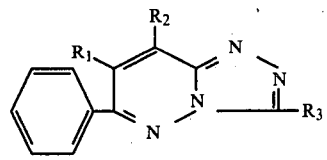

wherein $R_1$, $R_2$, and $R_3$ are each individually selected from the group consisting of hydrogen and alkyl having up to four carbon atoms with the first proviso that when $R_1$ and $R_2$ are both hydrogen then $R_3$ may not be methyl and with the second proviso that when $R_2$ and $R_3$ are both methyl then $R_1$ may not be hydrogen; and the pharmacologically acceptable acid-addition salts thereof.

2. A therapeutic composition in dosage unit form useful for meliorating anxiety in mammals comprising from about 0.03 milligram to about 10.0 milligrams per kilogram of body weight per daily dosage unit, in association with a pharmaceutical carrier, of a compound selected from the group consisting of those of the formula:

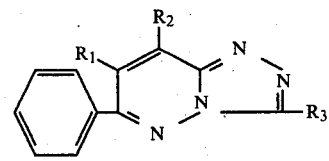

wherein $R_1$, $R_2$, and $R_3$ are each individually selected from the group consisting of hydrogen and alkyl having up to four carbon atoms with the first proviso that when $R_1$ and $R_2$ are both hydrogen then $R_3$ may not be methyl and with the second proviso that when $R_2$ and $R_3$ are both methyl then $R_1$ may not be hydrogen; and the pharmacologically acceptable acid-addition salts thereof.

* * * * *